(12) United States Patent
Andersson

(10) Patent No.: US 6,450,218 B1
(45) Date of Patent: Sep. 17, 2002

(54) FRACTION COLLECTOR

(75) Inventor: Lars Andersson, Uppsala (SE)

(73) Assignee: Amersham Pharmacia Biotech AB, Uppsala (SE)

( * ) Notice: Subject to any disclaimer, the term of this patent is extended or adjusted under 35 U.S.C. 154(b) by 0 days.

(21) Appl. No.: 09/775,958

(22) Filed: Feb. 2, 2001

(51) Int. Cl.[7] ............................ B65B 43/42; B67C 3/00
(52) U.S. Cl. ........................ 141/145; 141/144; 422/64
(58) Field of Search .................. 141/129, 130, 141/144, 145; 422/64, 100

(56) References Cited

U.S. PATENT DOCUMENTS 3,004,567 A * 10/1961 Snow et al. ............... 141/130
4,166,094 A * 8/1979 Froehlich et al. ............. 422/64

* cited by examiner

Primary Examiner—Timothy L. Maust
(74) Attorney, Agent, or Firm—Royal N. Ronning, Jr.; Stephen G. Ryan

(57) ABSTRACT

A fraction collector (1) for dispensing liquid from a liquid source into receptacles (23) carried on a rotatable turntable (6), wherein the turntable is connected to the fraction collector casing (5) via a support arm (7) such that the turntable is rotatably mounted at one end of said support arm, and said support arm at its other end being rotatably mounted to the fraction collector casing. Thereby it is possible to align any position of the turntable under a dispensing tube (4) to dispense a liquid into a receptacle placed anywhere on the turntable.

6 Claims, 5 Drawing Sheets

FRACTION COLLECTOR

FIELD OF THE INVENTION

The present invention relates to fraction collectors, such as fraction collectors used in the field of liquid chromatography.

DESCRIPTION OF RELATED ART

Numerous fraction collectors including a rotatably mounted turntable for supporting a plurality of collection tubes are known, for example through U.S. Pat. No. 4,862, 932. In fraction collectors of the turntable type, a liquid is sequentially discharged into the collection tubes through an outlet conduit, such as a hollow needle. The outlet conduit is mounted on an arm reaching over the turntable. Typically, the arm can swing around a vertical post to be positioned over different radial rows of collecting tubes.

Similarly, fraction collectors wherein collecting tubes are arranged in a rectangular grid pattern and an outlet conduit is positioned over each collecting tube by a rectilinear positioning movement are known. In such fraction collectors, herein referred to as "X-Y-collectors", it is usually the outlet conduit that is moved with respect to the collecting tubes. An example of such a fraction collector is shown in U.S. Pat. No. 4,422,151.

An example of an X-Y-collector wherein both a receptacle supporting table and a delivery head are moved linearly, in transverse directions with respect to each other, is described in U.S. Pat. No. 4,077,444.

In a conventional turntable fraction collector it is possible to dispense liquid volumes into a selected number of receptacles, for example test tubes. The dispensing means, typically a metal or plastic tube extending from an arm reaching over the receptacles, essentially is held at rest with respect to the turntable, while the receptacles change place by rotating the turntable when switching from one receiving receptacle to the next.

The turntable fraction collector is useful in many applications. However, in certain cases X-Y-collectors are more suitable. For example, when handling a large number of receptacles, bench space is more effectively used when arranging the receptacles in a X-Y-pattern. There are also popular standardized receptacle plates, so called microtiter plates, that have small recesses arranged in a X-Y-pattern. Conventional turntable fraction collectors cannot handle such plates.

A conventional X-Y-collector has a table for holding the receptacles (or microtiter plates or similar), and is further equipped with means for moving a dispensing tube over and between the receptacles. Typically, the moving of the dispensing tube is achieved by the use of a set of stepping motors. Furthermore, it is known to control the stepping motors to position the dispensing tube over any receptacle in any desired order.

However, compared to the turntable collector, a X-Y-collector requires a longer attachment tubing, since the equipment providing the liquid is stationary with respect to the receptacles, and the tubing therefore has to follow the dispensing tube to any receptacle. Especially in high-resolution liquid chromatography this is a disadvantage since a long tubing give separated components in the liquid longer time to diffuse within the liquid flow, and consequently the precision of the separation is negatively affected.

When switching from one receptacle to the next spillage could occur due to an outflow through the dispensing tube between the receptacles. Under certain conditions such spillage should be avoided, for example when collecting fractions of a liquid holding very valuable substances wherein it is important to collect each individual drop. In such cases, a conventional X-Y-collector is disadvantageous since the movement of the dispensing tube is apt to shake off any drop developed at the end of the dispensing tube during the switching movement.

The disadvantages of the conventional X-Y-collector, as described above, could be overcome with a X-Y-collector wherein the receptacle table is moved in the X and Y directions, instead of the dispensing tube. However, with such a construction valuable bench-space is lost.

SUMMARY OF THE INVENTION

It is the object of the present invention to provide a bench space saving fraction collector with the ability to position a selected receptacle among a plurality of receptacles, regardless of the pattern in which the receptacles are arranged, under a dispensing tube connected to a liquid feeding system This object is achieved with a device of the type described herein.

The fraction collector according to the invention combines the features of the substantially resting outlet tube, short attachment tubing length and small bench space requirement connected with a turntable collector, with the features of X-Y-arrangement ability and dispensing of liquid in a selectable sequence of receptacles connected with a X-Y-collector.

Thus, the fraction collector of the invention is useful for receptacles of any size (including of mutually different sizes) arranged in any two-dimensional pattern, eg. in circular rows of test tubes as well as microtiter plates.

Since the receptacles are moving during a receptacle change, rather than the dispensing tube, the risk of losing drops is reduced as compared to the conventional X-Y-collector.

As the dispensing tube is at rest with respect to the receptacles it can be positioned very near the outlet of any liquid feeding device, such as the outlet of a liquid chromatography column, thereby providing for the shortest possible attachment tubing.

All these advantageous features as well as others that are obvious from the following detailed description of preferred embodiments of the invention are obtained with a fraction collector requiring a limited amount of bench-space.

DETAILED DESCRIPTION OF PREFERRED EMBODIMENTS

Figure 1:
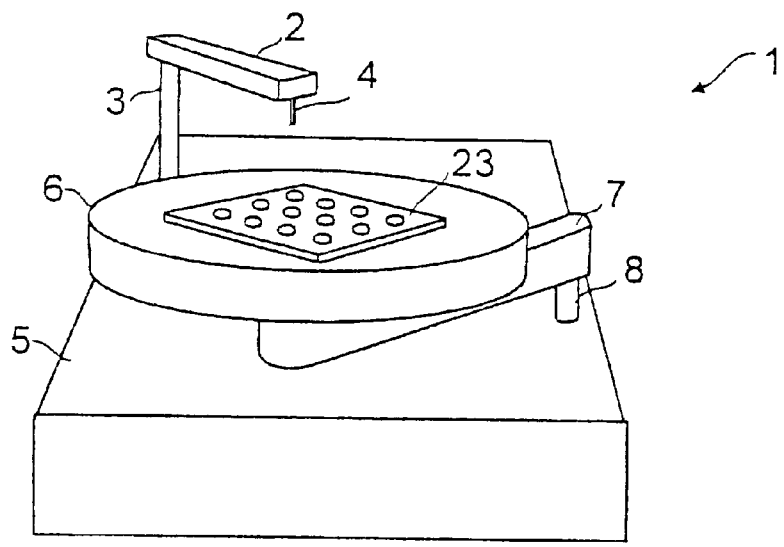
FIG. 1 is a schematical perspective front view of an embodiment of a fraction collector according to the present invention.
Figure 2:
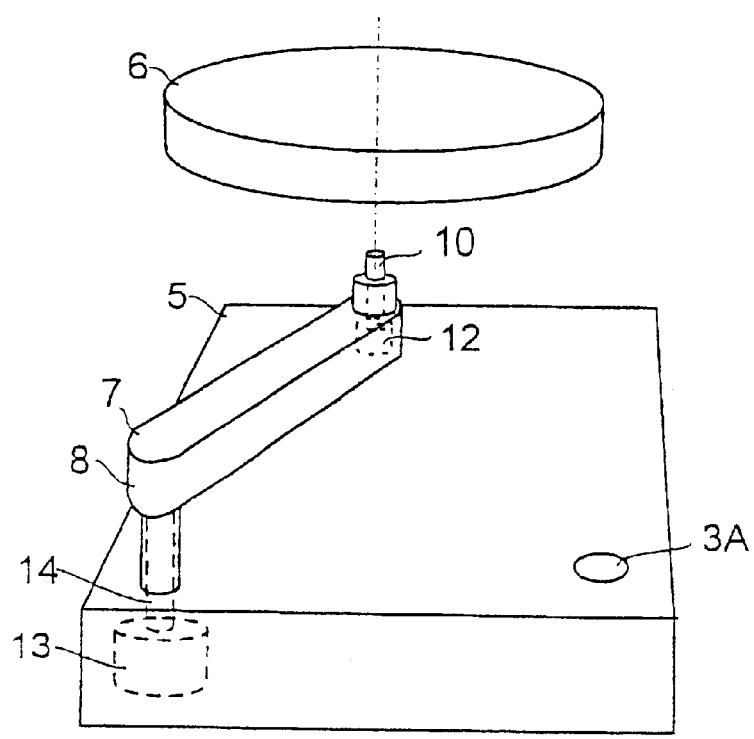
FIG. 2 is a partly exploded rear view of the fraction collector of FIG. 1.

An embodiment of a fraction collector 1 according to the present invention is shown in FIG. 1 and 2.

As is shown in FIG. 1, which is a perspective front view, the fraction collector includes a dispensing assembly including an extension arm 2 with a dispensing tube 4 mounted on a post 3, the post being supported on a fraction collector casing 5. Receptacles 23 (represented with a schematical microtiter plate 23) are placed on a turntable 6. The turntable is rotatably mounted on a support arm 7. The support arm 7 is rotatably mounted on the casing 5 via a supporting post 8. Connecting tubing and cables are not shown.

The arrangement is more clearly seen in FIG. 2, which is a partly exploded rear view wherein the extension arm assembly for reasons of clarity has been omitted and is symbolized by a hole 3A for receiving the arm 3. The center of the turntable 6 is fixed coupled to a first shaft 10.

The support arm 7 rotatably supports the first shaft 10 at one end of the arm. A first stepping motor 12 is mounted in the support arm 7, and is coupled to the first shaft 10. Thus, by driving the first stepping motor 12 the first shaft 10 is rotated and, in consequence, the turntable 6 is rotated therewith.

At its other end the support arm 7 is pivoted on the casing 5 via a tubular supporting post 8. A second shaft 14 extends through the supporting post 8 to couple the extension arm 7 to a second stepping motor 13 mounted in the casing 5. Thus, by driving the second stepping motor 13 the second shaft 14 is rotated and, in consequence, the support arm 7 is rotated therewith. As the support arm 7 swings, the turntable 6 and its shaft 10 and motor 12 swings therewith.

It should be noted that the detailed design of the components of the fraction collector, their positions, how to mount them in bearings etc. are not shown in detail. It is obvious for anyone skilled in the art that numerous designs of the separate components are possible, each one being well known in itself. Therefore, the detailed designs should be selected to suit the application at hand. This is also valid for the electric and electronic driving circuits, since it is easy to control the stepping motors (or any other suitable type of driving motors) according to the invention once the invention is understood.

During operation the extension arm 2 is at rest and, consequently, the dispensing tube is held still at a specific point with respect to the casing 5.

Figure 3:
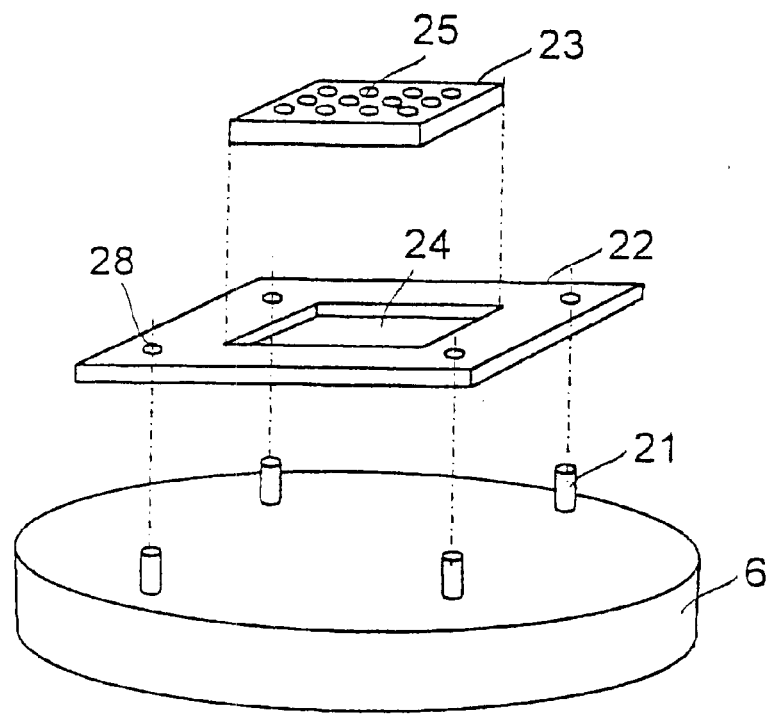
FIG. 3 is an exploded view of a template arrangement for placing a microtiter plate on the turntable of a fraction collector according to the present invention.

The receptacles are arranged on the turntable 6 in any selected pattern, but the position of each individual receptacle with respect to the turntable should be registered and input to a computer program for controlling the stepping motors 12, 13. Typically, a number of arrangements are pre-selected, and the corresponding receptacle positions are stored in a suitable computer data memory, such as a RAM, to be loaded at the operator's command. An easy way to arrange this is exemplified in FIG. 3, wherein a template 22 (being selected from a plurality of templates suited to different receptacle arrangements) has holes 28 that fit onto pins 21 inserted in the turntable to be positioned at a pre-selected position on the turntable. The template 22 has a recess 24 that is formed to receive a specific model of a microtiter plate 23 having a plurality of separate compartments 25. As the pin positions, the recess position and the size and positions of the compartments within the microtiter plate are known, the position of each compartment 25 with respect to the turntable 6 is easily determined in advance to be stored for use with the computer program.

When selecting the length and direction of the extension arm 2, as well as the position of the post 3 in the casing 5, care should be taken to ensure that the length of the arm 2 is enough to allow the turntable to pass under the arm free from the post 3. Furthermore, in order to ensure that all positions on the turntable are reachable for the tube 4, provided that this is a requirement, the tube should be positioned such that the first shaft 10 could be placed right below the tube.

According to the invention, by selecting the lengths of the extension arm 2, the support arm 7 and the turntable 6 radius for cooperation as described above, any position at the turntable can be positioned below the dispensing tube by suitably rotating the support arm 7 around the supporting post 8 while suitably rotating the turntable 6 with respect to the support arm 7.

This shall now be explained in more detail with reference to FIGS. 4–7, and using a small (non-standard) microtiter plate having four times three recessed compartments for receiving liquid. Such a plate 23 is shown in a top view in FIG. 4. Any compartment can be identified by its x-y-index, as defined in FIG. 4. As an example to be used throughout this explanation, the right uppermost (when viewing FIG. 4) compartment has the index x=4, y=3, and will therefore be referred to below as the (4, 3)-compartment. The compartments are separated in the x-direction with a distance D, and in the y-direction with the same distance D.

Figure 4:
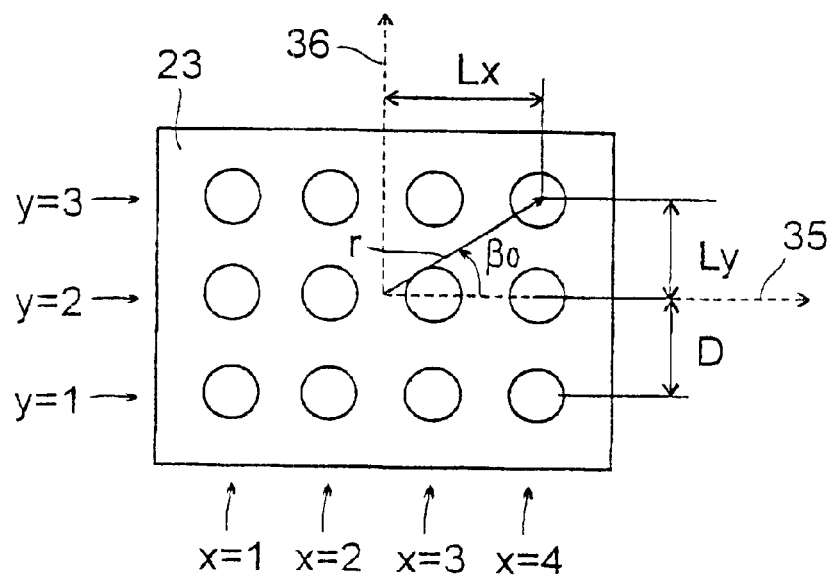
FIG. 4 is a top view of a set of receptacles in a microtiter plate, showing a system of coordinates associated with the plate.

A receptacle system of coordinates with its origin of coordinates in the center of the microtiter plate is defined by a receptacle x-axis 35 coinciding with the direction of the rows of compartments in the microtiter plate and a receptacle y-axis 36 extending perpendicularly with respect to the x-axis 35, as shown in FIG. 4. It is easily recognized that the x,y-position of the center of the exemplary (4, 3)-compartment with respect to the receptacle system of coordinates is (1.5*D, D).

The position can also be expressed in polar coordinates as $(r^*\cos(\beta o), r^*\sin(\beta o))$, wherein $r=(Lx^2+Ly^2)^{1/2}$ and $\beta o = \arccos(Lx/r)$.

Thus, the polar coordinates for the (4, 3)-compartment with respect to the receptacle system of coordinates is $((3.25)^{1/2}*D* \cos(\beta o), (3.25)^{1/2}*D* \sin(\beta o)$, wherein $\beta o = \arccos(1,5/(3.25)^{1/2})$.

Figure 5:
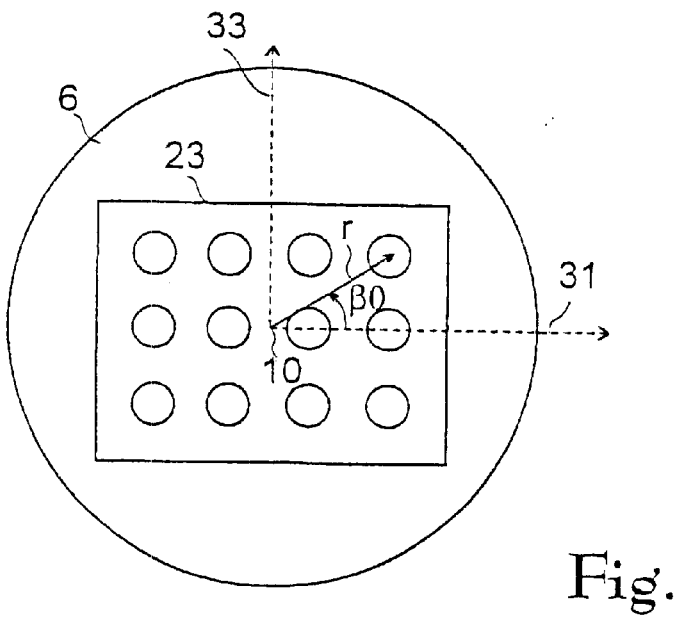
FIG. 5 is a top view of the plate according to FIG. 4 positioned on a turntable, showing a system of coordinates associated with the shaft rotating the turntable.

The microtiter plate 23 is positioned at the turntable 6 in such a way that the center of the microtiter plate, or more generally the origin of coordinates for the receptacle system of coordinates, coincides with an imagined extension of the central axis of the first shaft 10, as shown in FIG. 5. It is preferred to use a template, as described above, to ensure a correct positioning.

A turntable shaft system of coordinates, as shown in FIG. 5, with its origin of coordinates coinciding with a point at the extended central axis of the first shaft 10 is defined by a turntable x-axis 31 and a turntable y-axis 33 perpendicular with respect to the x-axis 31.

Figure 6:
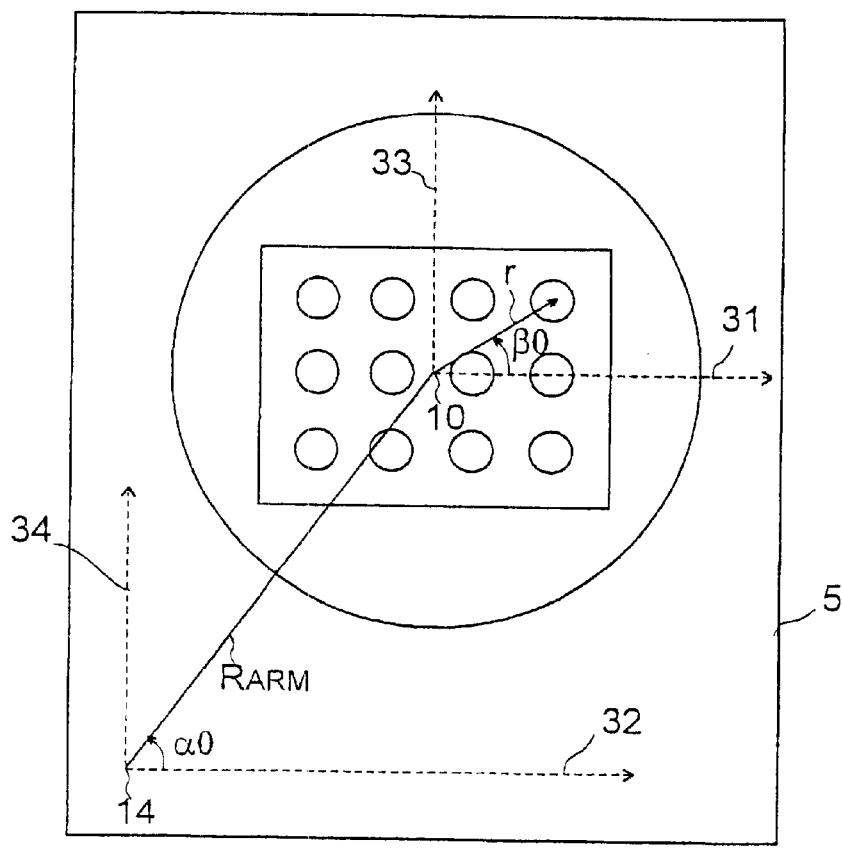
FIG. 6 is a top view of a fraction collector according to the invention, showing a system of coordinates associated with the fraction collector casing.

Furthermore, according to FIG. 6 a casing system of coordinates with its origin of coordinates coinciding with a point at the central axis of the second shaft 14 is defined by a casing x-axis 32 and a casing y-axis 34 perpendicular with respect to the casing x-axis 32.

The casing system of coordinates is fixed with respect to the casing 5. The origin of the turntable shaft system of coordinates follows the first shaft 10, but each axis is always parallel to the corresponding axis of the casing system of coordinates. That is, the turntable x-axis 31 is always parallel with the casing x-axis 32, although the origin of coordinates of the turntable shaft system of coordinates is moveable with respect to the casing system of coordinates.

A start position for the fraction collector according to the present embodiment of the invention is shown in FIG. 6. The center-to-center distance between the first and second shafts 10 and 14 is $R_{ARM}$. In the start position, the arm 7 is positioned at an angle $\alpha o$ with respect to the casing reference x-line 32. Similarly, in the start position the receptacle x-axis 35 (not being shown in FIG. 6) coincides with the turntable x-axis and is therefore parallel with the casing x-axis 32.

Thus, the start position of the center of the (4, 3)-compartment with respect to the casing system of coordinates is $$(R_{ARM}*\cos(\alpha o)+(3.25)^{1/2}*D*\cos(\beta o), R_{ARM}*\sin(\alpha o)+(3.25)^{1/2}*D*\sin(\beta o))$$

Figure 7:
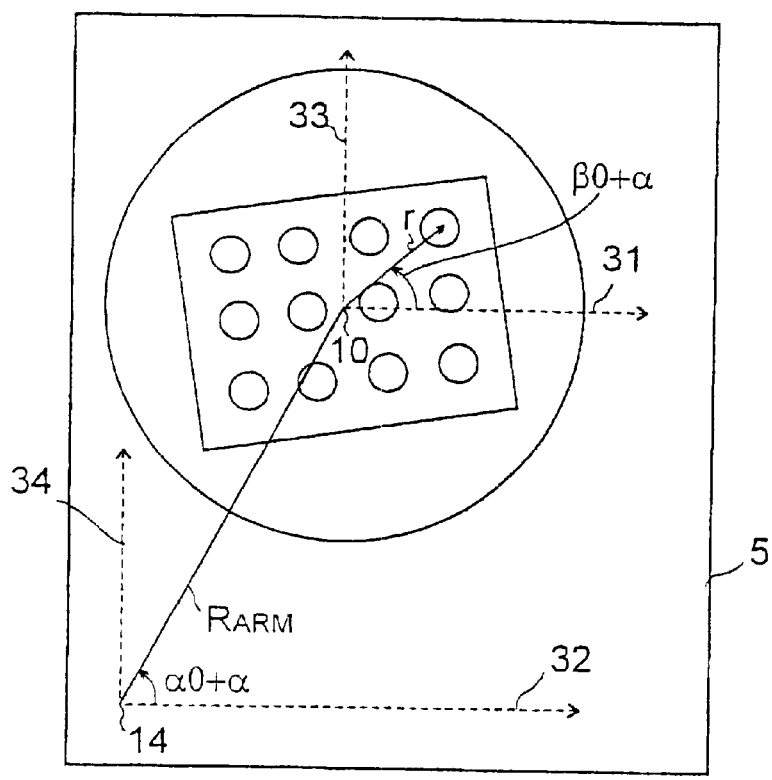
FIG. 7 is a top view of the fraction collector according to FIG. 6, after rotating the support arm.

FIG. 7 shows a position after that the arm 7 has been rotated around the second shaft 14 an angle $\alpha$ with respect to the casing system of coordinates, to be positioned at a new angle $\alpha 1$ with respect to the casing system of coordinates ($\alpha 1=\alpha o+\alpha$). During the movement of the arm 7, the first axis 10 has been held at rest with respect to the support arm 7. Therefore, the receptacle system of coordinates will no longer coincide with the turntable shaft system of coordinates, but will be rotated with respect to the turntable shaft system by the same angle $\alpha$ that the arm 7 has been rotated.

Figure 8:
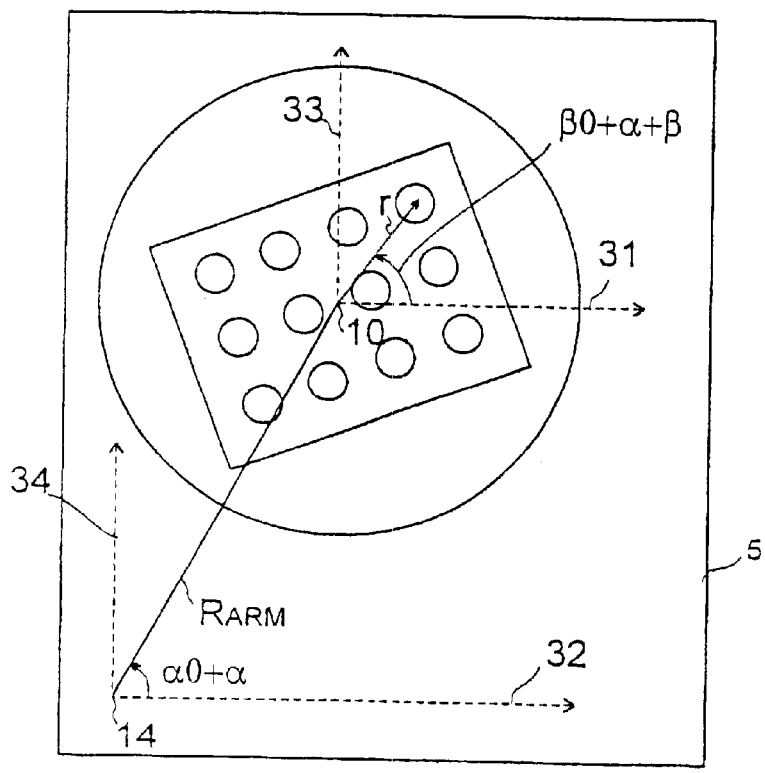
FIG. 8 is a top view of the fraction collector according to FIG. 7, after rotating the turntable.

If, in addition thereto, the first shaft 10 is rotated an angle $\beta$ with respect to the support arm 7, the receptacle system of coordinates is also rotated the angle $\beta$ with respect to the turntable system of coordinates and, consequently, also with respect to the casing system of coordinates. This is shown in FIG. 8. In summary, the receptacle system of coordinates is now at an angle of $\beta 1=(\beta o+\alpha+\beta)$ with respect to the casing system Therefore, after rotating the first shaft 10 to the angle $\alpha 1$, with respect to the casing system of coordinate, and the second shaft the angle $\beta 1$ with respect to the support arm, the center of the (4, 3)-compartment is now at the point $(R_{ARM}*\cos(\alpha 1)+(3.25)^{1/2}*D*\cos(\beta 1), R_{ARM}*\sin(\alpha 1)+(3.25)^{1/2}*D*\sin(\beta 1))$ with respect to the casing system of coordinates Thus, starting from a first position for a separate receptacle, the receptacle can be positioned anywhere within an annular area surrounding the second shaft 14, the annular area having an inner radius of ($R_{ARM}-r$) and an outer radius of ($R_{ARM}+r$), provided that no obstacles are placed within the area. This means that in the case that the dispensing tube 4 is positioned anywhere on the circle representing the radius $R_{ARM}$ around the second shaft 14, it is possible to align any receptacle on the turntable under the tube 4.

The receptacles could be arranged according to any pattern on the turntable, as long as their initial positions with respect to the turntable are known, and a computer program used for controlling the operation of the fraction collector is updated with the present positions. For example, more than one microtiter plate could be placed on the turntable.

In operation, a computer program can be used to control the rotation of the first and second shafts via a control unit. Since anyone skilled in the art is able to design a control unit and a suitable computer program to suit a certain embodiment of a fraction collector according to the invention, this will not be described in detail.

However, for each receptacle to be filled, and in any selected order, the turntable is rotated to place the receptacle under the dispensing tube. Accordingly, the position of the dispensing tube 4 ($X_{DT}$, $Y_{DT}$) with respect to the casing system of coordinates has to be known and input to the controlling computer program.

Figure 9:
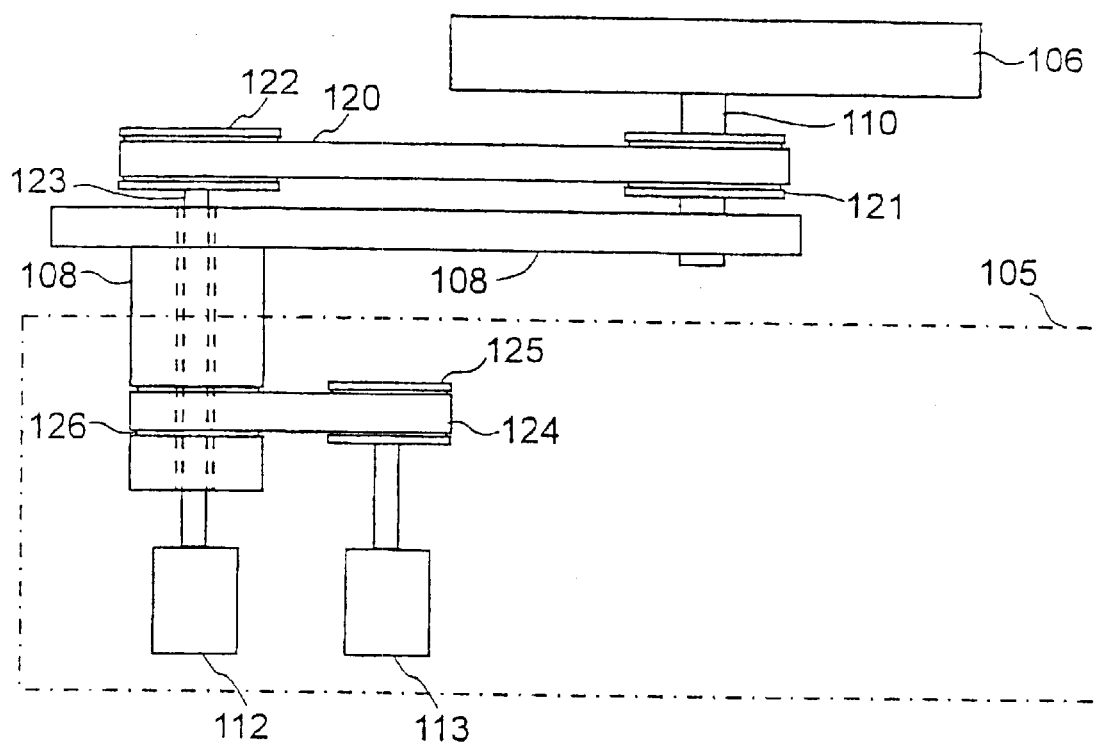
FIG. 9 is a schematical side view showing a belt transmission for use with an embodiment of the present invention.

A second embodiment of the present invention, as shown schematically in FIG. 9, differs from the first embodiment in that the motor 112 rotating the turntable 106 is mounted within the casing 105, instead of being mounted in the support arm 107. With this arrangement the support arm is relieved from the weight of the motor, and no electrical wires need to be guided through the support arm.

The rotation of the turntable driving motor 112 is transferred to the turntable 106 via a first belt 120 running around a first belt pulley 121 attached to the first shaft 110 of the turntable and a second belt pulley 122 attached to a drive shaft 123 being driven by the turntable driving stepping motor 112.

The first shaft 110 is mounted in a bearing (not shown) in the free end of the support arm 107, while the drive shaft 123 runs through a tubular post 108 fixedly attached to the support arm 107 and mounted in bearings (not shown) in the casing.

A second belt 124, that runs around a belt groove 126 in the tubular post 108 and a belt pulley 125 attached to the drive shaft of a second stepping motor 113, the second motor being mounted within the casing 105, transfers the rotation of the second motor to the tubular post, thereby rotating the support arm.

It should be noted that the illustration of the second embodiment, as shown in FIG. 9, is schematical in that no details of the attaching means are shown. It is of course obvious for anyone skilled in the art that the components that form the second embodiment could be formed and assembled in numerous ways, each one selected to suit the application at hand. Of course, the rotating movement could be transferred to the turntable by any suitable means other than a belt transmission, such as a chain transmission, a gear transmission or a universal drive shaft.

In addition to the advantages described above for a fraction collector according to the present invention even more advantages could be obtained. For example, minimal band broadening related to the separation of fractions within the outlet tubing before the dispensing means is achievable due to the short tubing. The non-moving dispensing tube support makes it possible to attach a detector, such as an UV detector at a favorable position near the dispensing means. Furthermore, faster tube shifting is possible since no drops are lost due to dispensing means movement.

It is obvious for anyone skilled in the art that many variations of the invention are possible within the scope of the invention. Such variations include, but are not limited to, the type of driving means for the shafts (such as DC motors with gear boxes), the position of the motors (such as mounting a stepping motor in the turntable, or mounting both motors in the support arm), using one stepping motor only to drive both the turntable and the support arm, providing the dispensing tube in a separate stand free from the fraction collector etc. The specific embodiments described are given by way of example only, and the invention is limited only by the terms of the appended claims.

What is claimed is:

1. A fraction collector (1) for dispensing liquid from a liquid source into receptacles (25) carried on a turntable (6, 106) being rotatable with respect to a fraction collector casing (5, 105), comprising:

the turntable (6, 106) connected to the fraction collector casing (5, 105) via a support arm (7, 107) having two ends, the turntable being rotatably mounted at one end of said support arm, and said support arm at its other end being rotatably mounted to the fraction collector casing.

2. The fraction collector of claim 1, wherein the fraction collector further comprises a stepping motor (12, 112) for rotating the turntable with respect to said support arm (7, 107).

3. The fraction collector of claim 2, wherein said stepping motor (12) is mounted in said support arm (7).

4. The fraction collector of claim 2, wherein said stepping motor (112) is mounted in the fraction collector casing (105), and includes a belt drive which transfers the rotation of said stepping motor to the turntable (106) via said support arm (107).

5. The fraction collector of claim 2, which further includes a second stepping motor (13, 113) provided in the casing (5, 105) of the fraction collector for rotating said support arm (7, 107) with respect to the casing.

6. The fraction collector of claim 1, wherein said first and second end of said support arm respectively pivot about each other.

\* \* \* \* \*